US010984241B2

(12) United States Patent
Ota et al.

(10) Patent No.: US 10,984,241 B2
(45) Date of Patent: Apr. 20, 2021

(54) MEDICAL IMAGE DIAGNOSIS APPARATUS AND MAGNETIC RESONANCE IMAGING APPARATUS

(71) Applicant: Canon Medical Systems Corporation, Otawara (JP)

(72) Inventors: Miyuki Ota, Otawara (JP); Mitsuo Takagi, Otawara (JP); Sadanori Tomiha, Nasushiobara (JP); Satoshi Imai, Nasushiobara (JP); Masahiro Fukushima, Utsunomiya (JP); Manabu Ishii, Otawara (JP); Shinji Mitsui, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 96 days.

(21) Appl. No.: 15/960,704

(22) Filed: Apr. 24, 2018

(65) Prior Publication Data

US 2018/0314891 A1   Nov. 1, 2018

(30) Foreign Application Priority Data

Apr. 27, 2017   (JP) .............................. JP2017-088530

(51) Int. Cl.
*G06K 9/00* (2006.01)
*G06T 7/70* (2017.01)
(Continued)

(52) U.S. Cl.
CPC ....... *G06K 9/00671* (2013.01); *G01R 33/543* (2013.01); *G01R 33/5608* (2013.01);
(Continued)

(58) Field of Classification Search
CPC .................................................. G06K 9/00671
See application file for complete search history.

(56) References Cited

U.S. PATENT DOCUMENTS

2008/0027306 A1*  1/2008  Washburn .............. A61B 6/032
                                                            600/410
2013/0342350 A1   12/2013  Popescu
(Continued)

FOREIGN PATENT DOCUMENTS

| JP | 2014-004364 | 1/2014 |
| JP | 2014-155207 A | 8/2014 |
| JP | 2015-043920 | 3/2015 |

OTHER PUBLICATIONS

Japanese Office Action dated Feb. 16, 2021, issued in Japanese Patent Application No. 2017-088530.

*Primary Examiner* — Oneal R Mistry
(74) *Attorney, Agent, or Firm* — Oblon, McClelland, Maier & Neustadt, L.L.P.

(57) ABSTRACT

A medical image diagnosis apparatus according to an embodiment includes a storage circuitry and processing circuitry. The storage circuitry is configured to store therein workflow information indicating a plurality of procedures related to a preparation for an imaging process. The processing circuitry is configured to analyze an image obtained by a camera. The processing circuitry is configured to identify which of the plurality of procedures has been performed on the basis of the workflow information and a result of the analysis performed on the image and to cause an informing device to provide information about one or more of the procedures corresponding to a result of the identifying.

20 Claims, 5 Drawing Sheets

(51) Int. Cl.
    *H04N 9/31*       (2006.01)
    *G01R 33/56*      (2006.01)
    *G01R 33/54*      (2006.01)
    *G16H 30/20*      (2018.01)
    *G16H 50/20*      (2018.01)
    *G16H 30/40*      (2018.01)
    *G16H 40/63*      (2018.01)
    *G01R 33/28*      (2006.01)
    *G06F 3/147*      (2006.01)

(52) U.S. Cl.
    CPC ............... *G06T 7/70* (2017.01); *G16H 30/20* (2018.01); *G16H 30/40* (2018.01); *G16H 40/63* (2018.01); *G16H 50/20* (2018.01); *H04N 9/3147* (2013.01); *H04N 9/3185* (2013.01); *G01R 33/283* (2013.01); *G06F 3/147* (2013.01); *G06K 2209/057* (2013.01); *G06T 2207/30196* (2013.01)

(56) References Cited

U.S. PATENT DOCUMENTS

| | | | | |
|---|---|---|---|---|
| 2014/0364720 | A1* | 12/2014 | Darrow | A61B 5/748 |
| | | | | 600/410 |
| 2014/0378816 | A1* | 12/2014 | Oh | G01R 33/546 |
| | | | | 600/409 |
| 2017/0143271 | A1* | 5/2017 | Gustafsson | G01R 33/283 |
| 2017/0156630 | A1* | 6/2017 | Gabr | A61B 5/0013 |
| 2017/0168124 | A1* | 6/2017 | Ueda | A61B 5/0035 |
| 2018/0200018 | A1* | 7/2018 | Silva | A61B 34/20 |
| 2018/0271396 | A1* | 9/2018 | Watts | A61B 5/0064 |

* cited by examiner

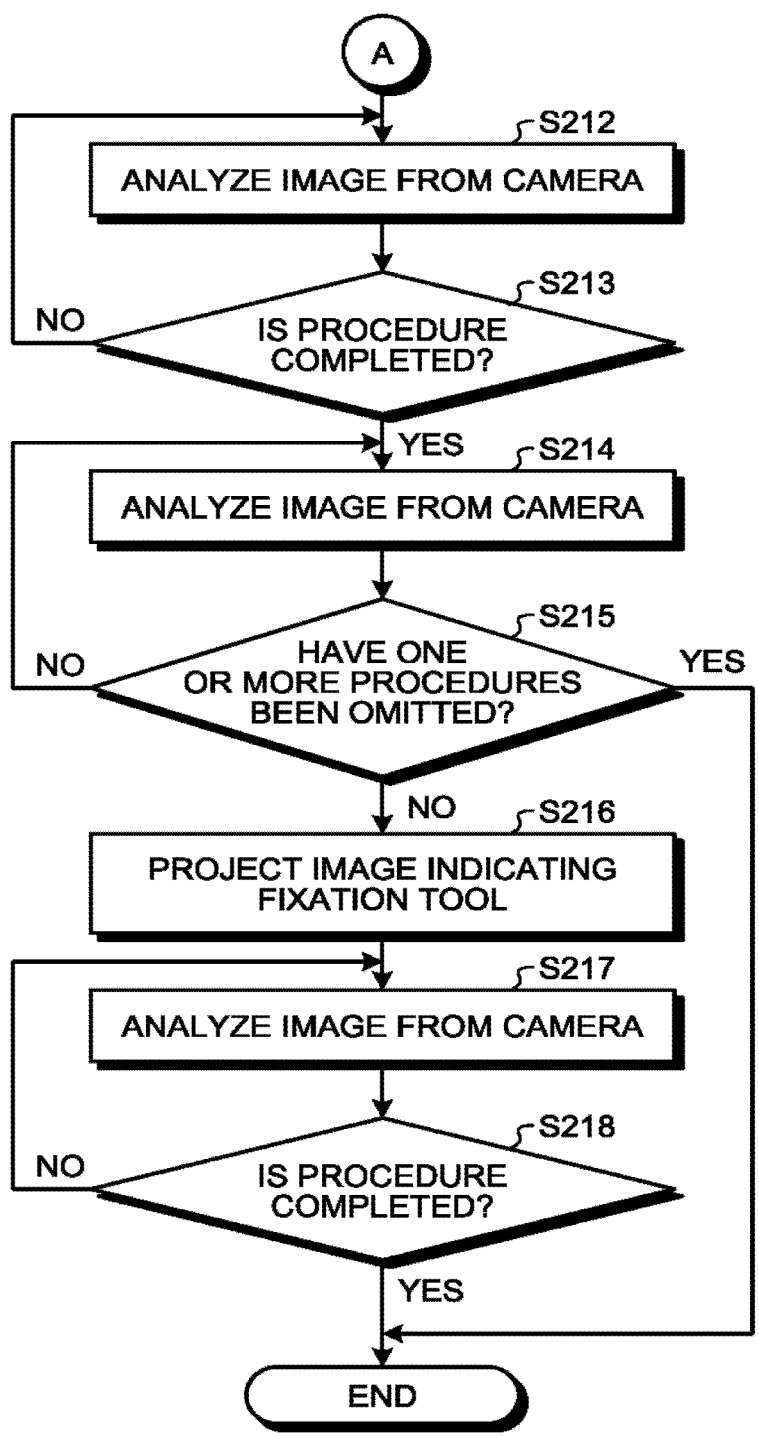

MEDICAL IMAGE DIAGNOSIS APPARATUS AND MAGNETIC RESONANCE IMAGING APPARATUS

CROSS-REFERENCE TO RELATED APPLICATIONS

This application is based upon and claims the benefit of priority from Japanese Patent Application No. 2017-088530, filed on Apr. 27, 2017; the entire contents of which are incorporated herein by reference.

FIELD

Embodiments described herein relate generally to a medical image diagnosis apparatus and a magnetic resonance imaging apparatus.

BACKGROUND

Conventionally, some medical image diagnosis apparatuses such as Magnetic Resonance Imaging (MRI) apparatuses and X-ray Computed Tomography (CT) apparatuses require a large amount of information when performing imaging processes. For example, a magnetic resonance imaging apparatus requires information indicating a method for selecting tools used for an imaging process such as a Radio Frequency (RF) coil, a pad, and the like, as well as a method for setting the examined subject. For this reason, for example, methods are known by which methods for operating the apparatus are indicated in an instruction manual or methods for operating the apparatus are displayed on a display device of the medical image diagnosis apparatus.

BRIEF DESCRIPTION OF THE DRAWINGS

FIG. 5 is another flowchart illustrating the example of the process performed by the MRI apparatus according to the modification example of the present embodiment.

DETAILED DESCRIPTION

A medical image diagnosis apparatus according to an embodiment includes a storage unit, an analyzing unit, and an informing unit. The storage unit is configured to store therein workflow information indicating a plurality of procedures related to a preparation for an imaging process. The analyzing unit is configured to analyze an image obtained by a camera. The informing unit is configured to identify which of the plurality of procedures has been performed on the basis of the workflow information and a result of the analysis performed on the image and to cause an informing device to provide information about one or more of the procedures corresponding to a result of the identifying.

Exemplary embodiments of a medical image diagnosis apparatus will be explained below, with reference to the accompanying drawings. In the following sections, application examples related to MRI apparatuses will be explained, as examples of the medical image diagnosis apparatus.

Embodiments

Figure 1:
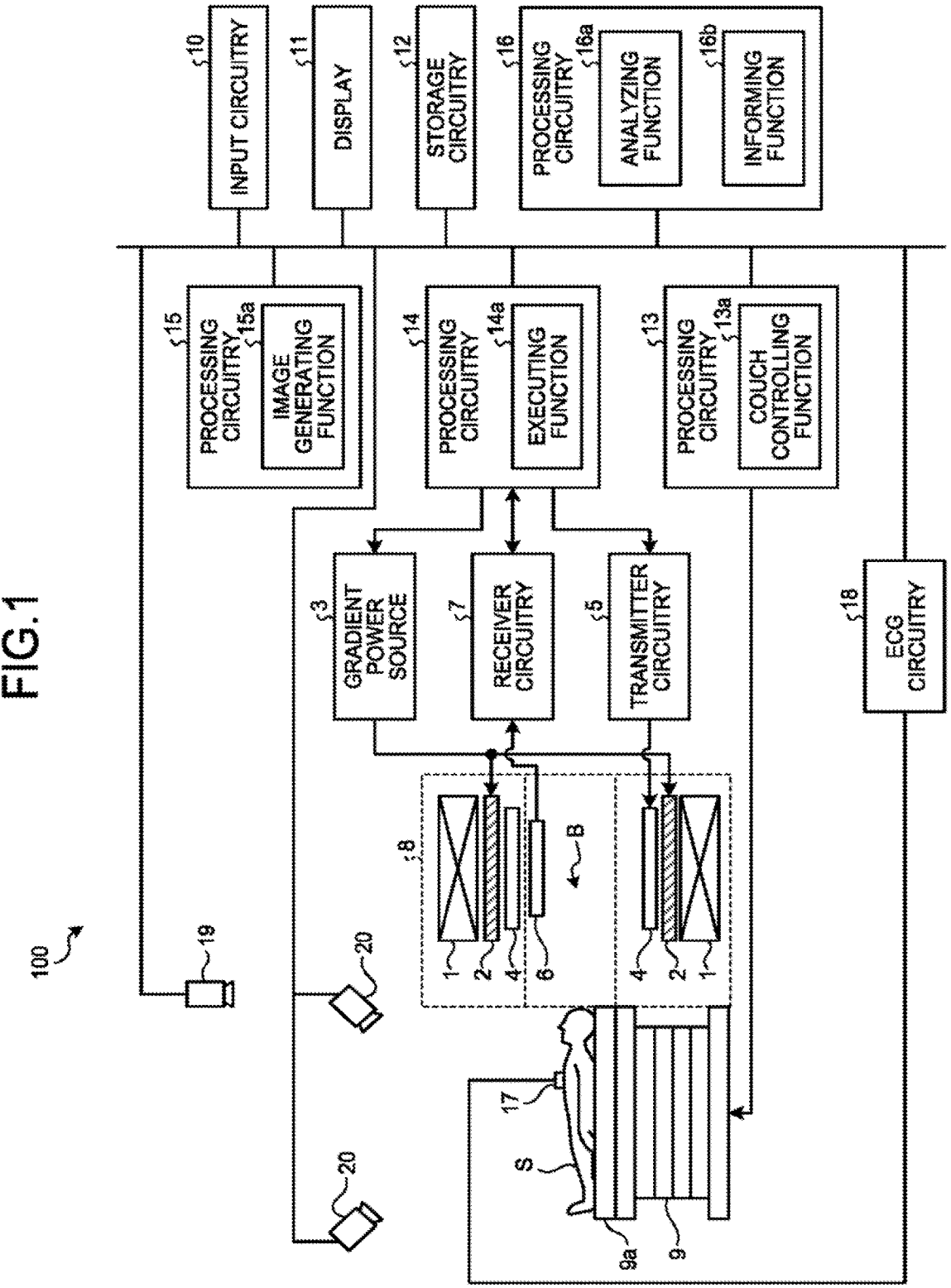
FIG. 1 is a diagram illustrating an exemplary configuration of an MRI apparatus according to an embodiment.

FIG. 1 is a diagram illustrating an exemplary configuration of an MRI apparatus according to an embodiment. For example, as illustrated in FIG. 1, an MRI apparatus 100 according to an embodiment includes a static magnetic field magnet 1, a gradient coil 2, a gradient power source 3, a transmitter coil 4, a transmitter circuitry 5, a receiver coil 6, a receiver circuitry 7, a gantry 8, a couch 9, an input circuitry 10, a display 11, a storage circuitry 12, and pieces of processing circuitry 13 to 16; an electrocardiogram (ECG) sensor 17; an ECG circuitry 18, a camera 19, and one or more projectors 20.

The static magnetic field magnet 1 is formed to have a hollow and substantially circular cylindrical shape (which may have an oval cross-section orthogonal to the central axis thereof) and is configured to generate a static magnetic field in the space on the inside thereof. For example, the static magnetic field magnet 1 includes a cooling container formed to have a substantially circular cylindrical shape and a magnet such as a superconductive magnet that is immersed in a cooling material (e.g., liquid helium) filling the cooling container. Alternatively, for example, the static magnetic field magnet 1 may be configured to generate the static magnetic field by using a permanent magnet. Further, instead of being formed to have the substantially circular cylindrical shape, the static magnetic field magnet 1 may have a so-called open structure, for example, where a pair of magnets are arranged to face each other, while having interposed therebetween an imaging space in which an examined subject (hereinafter, "patient") S is placed.

The gradient coil 2 is formed to have a hollow and substantially circular cylindrical shape (which may have an oval cross-section orthogonal to the central axis thereof) and is disposed on the inside of the static magnetic field magnet 1. The gradient coil 2 includes three coils configured to generate gradient magnetic fields along x-, y-, and z-axes, respectively, that are orthogonal to one another. In this situation, the x-axis, the y-axis, and the z-axis structure an apparatus coordinate system unique to the MRI apparatus 100. For example, the x-axis direction is set in the horizontal direction, whereas the y-axis direction is set in the vertical direction. Further, z-axis direction is set so as to be the same as the direction of a magnetic flux in the static magnetic field generated by the static magnetic field magnet 1.

By individually supplying an electric current to each of the three coils included in the gradient coil 2, the gradient power source 3 is configured to cause the gradient magnetic fields to be generated along the x-, y-, and z-axes, respectively, in the space formed inside the gradient coil 2. The gradient power source 3 is able to cause the gradient magnetic fields to be generated along a read-out direction, a phase-encoding direction, and a slice direction, by generating the gradient magnetic fields along the x-, y-, and z-axes, as appropriate.

In this situation, the axes extending along the read-cut direction, the phase-encoding direction, and the slice direction structure a logical coordinate system used for defining slice regions or a volume region serving as a target of an imaging process. In the following sections, the gradient magnetic field generated along the read-out direction will be referred to as a read-out gradient magnetic field; the gradient magnetic field generated along the phase-encoding direction will be referred to as a phase-encoding gradient magnetic field; and the gradient magnetic field generated along the slice direction will be referred to as a slice gradient magnetic field.

Further, the gradient magnetic fields are superimposed on the static magnetic field generated by the static magnetic field magnet 1 and are used for appending spatial position information to magnetic resonance (MR) signals. More specifically, the read-out gradient magnetic field appends position information along the read-out direction to an MR signal, by varying the frequency of the MR signal in accordance with the position in the read-cut direction. Further, the phase-encoding gradient magnetic field appends position information in the phase-encoding direction to an MR signal, by varying the phase of the MR signal along the phase-encoding direction. Further, when an imaging region is represented by slice regions, the slice gradient magnetic field is used for determining the orientations, the thicknesses, and the quantity of the slice regions. In contrast, when the imaging region is represented by a volume region, the slice gradient magnetic field appends position information along the slice direction to an MR signal, by varying the phase of the MR signal in accordance with the position in the slice direction.

The transmitter coil 4 is a Radio Frequency (RF) coil configured to apply an RF magnetic field to the space on the inside thereof. More specifically, the transmitter coil 4 is formed to have a hollow and substantially circular cylindrical shape (which may have an oval cross-section orthogonal to the central axis thereof) and is disposed on the inside of the gradient oil 2. Further, on the basis of an RF pulse output from the transmitter circuitry 5, the transmitter coil 4 is configured to apply the RF magnetic field to the space on the inside thereof.

The transmitter circuitry 5 is configured to output the RF pulse corresponding to a Larmor frequency to the transmitter coil 4. For example, the transmitter circuitry 5 includes an oscillation circuit, a phase selecting circuit, a frequency converting circuit, an amplitude modulating circuit, and a radio frequency amplifying circuit. The oscillation circuit is configured to generate the RF pulse having a resonant frequency unique to a targeted atomic nucleus placed in the static magnetic field. The phase selecting circuit is configured to select a phase of the RF pulse output from the oscillation circuit. The frequency converting circuit is configured to convert the frequency of the RF pulse output from the phase selecting circuit. The amplitude modulating circuit is configured to modulate the amplitude of the RF pulse output from the frequency converting circuit, according to a sinc function, for example. The radio frequency amplifying circuit is configured to amplify the RF pulse output from the amplitude modulating circuit and to output the amplified RF pulse to the transmitter coil 4.

The receiver coil 6 is an RF coil configured to receive MR signals emitted from the patient S. For example, the receiver coil 6 is attached to the patient S placed on the inside of the transmitter coil 4 and is configured to receive the MR signals emitted from the patient S due to an influence of the RF magnetic fields applied by the transmitter coil 4. Further, the receiver coil 6 is configured to output the received MR signals to the receiver circuitry 7. For example, as the receiver coil 6, a coil dedicated for each of the various sites serving as targets of imaging processes is used. In this situation, examples of the coils dedicated for the various sites include a receiver coil for the head, a receiver coil for the neck, a receiver coil for a shoulder, a receiver coil for the chest, a receiver coil for the abdomen, a receiver coil for a leg, and a receiver coil for the spine.

The receiver circuitry 7 is configured to generate MR signal data on the basis of the MR signals output from the receiver coil 6 and to output the generated MR signal data to the processing circuitry 14. For example, the receiver circuitry 7 includes a selecting circuit, a pre-amplifying circuit, a phase detecting circuit, and an analog-to-digital converting circuit. The selecting circuit is configured to selectively receive an input of the MR signals output from the receiver coil 6. The pre-amplifying circuit is configured to amplify the MR signals output from the selecting circuit. The phase detecting circuit is configured to detect the phases of the MR signals output from the pre-amplifying circuit. The analog-to-digital converting circuit is configured to generate the MR signal data by converting analog signals output from the phase detecting circuit into digital signals and to output the generated MR signal data to the processing circuitry 14.

In the present example, the situation in which the transmitter coil 4 applies the RF magnetic field so that the receiver coil 6 receives the MR signals is explained; however, possible embodiments of the RF coils are not limited to this example. For instance, the transmitter coil 4 may further have a receiving function to receive the MR signals. Further, the receiver coil 6 may further have a transmitting function to apply the RF magnetic field. When the transmitter coil 4 has the receiving function, the receiver circuitry generates MR signal data also from the MR signals received by the transmitter coil 4. Further, when the receiver coil has the transmitting function, the transmitter circuitry 5 outputs an RF pulse also to the receiver coil 6.

The gantry 8 houses therein the static magnetic field magnet 1, the gradient coil 2, and the transmitter coil 4. More specifically, the gantry 8 has a bore B that is hollow and is formed to have a circular cylindrical shape. While the static magnetic field magnet 1, the gradient coil 2, and the transmitter coil 4 are disposed so as to surround the bore B, the gantry 8 houses therein the static magnetic field magnet 1, the gradient coil 2, and the transmitter coil 4. In this situation, the space on the inside of the bore B of the gantry 8 corresponds to the imaging space in which the patient S is placed when an imaging process is performed on the patient S.

The couch 9 includes a couchtop 9a on which the patient S is placed. When an imaging process is performed on the patient S, the couchtop 9a is inserted to the inside of the bore B of the gantry 8. For example, the couch 9 is installed in such a manner that the longitudinal direction thereof extends parallel to the central axis of the static magnetic field magnet 1.

The input circuitry 12 is configured to receive operations to input various types of instructions and various types of information from the operator. More specifically, the input circuitry 10 is connected to the processing circuitry 16 and is configured to convert the input operations received from the operator into electrical signals and to output the electrical signals to the processing circuitry 16. For example, the input circuitry 10 is realized with a trackball, a switch button, a mouse, a keyboard, a touch panel, and/or the like.

The display 11 is configured to display various types of information and various types of images. More specifically, the display 11 is connected to the processing circuitry 16 and is configured to convert the various types of information and data of the various types of images sent thereto from the processing circuitry 16, into display-purpose electrical signals and to output the display-purpose electrical signals. For example, the display 11 is realized with a liquid crystal monitor, a Cathode Ray Tube (CRT) monitor, a touch panel, or the like.

The storage circuitry 12 is configured to store various types of data therein. For example, the storage circuitry 12 is configured to store therein the MR signal data and image data. For example, the storage circuitry 12 is realized with a semiconductor memory device such as a Random Access Memory (RAM), a flash memory, or the like, or a hard disk, an optical disk, or the like.

The processing circuitry 13 includes a couch controlling function 13a. For example, the processing circuitry 13 is realized with a processor. The couch controlling function 13a is connected to the couch 9 and is configured to control operations of the couch 9 by outputting a control-purpose electrical signal to the couch 9. For example, the couch controlling function 13a receives, via the input circuitry 10, an instruction to move the couchtop 9a in a longitudinal direction, an up-and-down direction, or a left-and-right direction from the operator and operates a driving mechanism for the couchtop 9a included in the couch 9 so as to move the couchtop 9a according to the received instruction.

The processing circuitry 14 includes an executing function 14a. For example, the processing circuitry 14 is realized with a processor. The executing function 14a is configured to perform a data acquisition to acquire the MR signal data by driving the gradient power source 3, the transmitter circuitry 5, and the receiver circuitry 7, on the basis of sequence execution data output from the processing circuitry 16.

In this situation, the sequence execution data is information that defines a pulse sequence indicating a procedure performed to acquire the MR signal data. More specifically, the sequence execution data is information that defines: the timing with which the electric current is to be supplied from the gradient power source 3 to the gradient coil 2 and the intensity of the electric current to be supplied; the intensity of the RF pulse to be supplied from the transmitter circuitry 5 to the transmitter coil 4 and the timing with which the RF pulse is to be supplied; the timing with which the MR signals are to be detected by the receiver circuitry 7, and the like.

Further, the executing function 14a is configured to receive the MR signal data from the receiver circuitry 7 as a result of executing various types of pulse sequences and to store the received MR signal data into the storage circuitry 12. A set made up of pieces of MR signal data received by the executing function 14a is stored in the storage circuitry 12 as data structuring a k-space as a result of being arranged two-dimensionally or three-dimensionally according to the position information appended by the read-out gradient magnetic field, the phase-encoding gradient magnetic field, and the slice gradient magnetic field described above.

The processing circuitry 15 includes an image generating function 15a. For example, the processing circuitry 15 is realized with a processor. The image generating function 15a is configured to generate an image on the basis of the MR signal data stored in the storage circuitry 12. More specifically, the image generating function 15a generates the image by reading the MR signal data stored into the storage circuitry 12 by the executing function 14a and further performing a reconstructing process such as a post-processing process (i.e., a Fourier transform or the like) on the read MR signal data. Further, the image generating function 15a stores image data of the generated image into the storage circuitry 12.

The processing circuitry 16 is configured to exercise overall control of the MRI apparatus 100 by controlling constituent elements of the MRI apparatus 100. For example, the processing circuitry 16 is realized with a processor. For example, the processing circuitry 16 receives an imaging condition (e.g., an input of various types of parameters related to the pulse sequence) from the operator via the input circuitry 10 and generates the sequence execution data on the basis of the received imaging condition. After that, the processing circuitry 16 controls the data acquisition to acquire the MR signal data, by transmitting the generated sequence execution data to the processing circuitry 14. Further, for example, the processing circuitry 16 reads the image data of an image requested by the operator from the storage circuitry 12 and outputs the read image to the display 11.

The ECG sensor 17 is attached to the body surface of the patient S and is configured to detect an electrocardiograph signal of the patient S. After that, the ECG sensor 17 outputs the detected electrocardiograph signal to the ECG circuitry 18.

The ECG circuitry 18 is configured to detect a predetermined electrocardiographic waveform on the basis of the electrocardiograph signal output from the ECG sensor 17. For example, the FCC circuitry 18 is configured to detect an R-wave as the predetermined electrocardiographic waveform. After that, the ECG circuitry 18 generates a trigger signal at the time when the predetermined electrocardiographic waveform is detected and outputs the generated trigger signal to the processing circuitry 16. In this situation, the trigger signal may be transmitted from the ECG circuitry 18 to the processing circuitry 16 by wireless communication.

The camera 19 is installed in an imaging room in which the MRI apparatus 100 is provided and is configured to obtain an image of an area including the MRI apparatus 100 and the surroundings of the MRI apparatus 100. In this situation, the camera 19 is configured to obtain a moving image of the area including the MRI apparatus 100 and the surroundings of the MRI apparatus 100. Further, the camera 19 is connected to the processing circuitry 16 and is configured to output the obtained image to the processing circuitry 16. In addition, for example, the camera 19 may further be installed in a passage to the imaging room, a room in which a preparation for the imaging process is performed, and/or the like.

The one or more projectors 20 are installed in the imaging room in which the MRI apparatus 100 is provided and are configured to project a picture onto an area including the MRI apparatus 100 and the surroundings of the MRI apparatus 100. More specifically, two or more projectors 20 are installed in the imaging room, and each of the projectors 20 is connected to the processing circuitry 16. Further, each of the projectors 20 is configured to project a picture output from the processing circuitry 16 onto the MRI apparatus 100, a tool used for the imaging process, the patient S, or the operator T.

An exemplary configuration of the MRI apparatus 100 according to the present embodiment has thus been explained. Generally speaking, MRI apparatuses may require information indicating a method for selecting tools (e.g., an RF coil, a pad, etc.) used for imaging processes and/or a method for setting the patient, depending on the level of skills and experience of the operator. For this reason, for example, methods are known by which an operation method is displayed on a display device or the like of a medical image diagnosis apparatus. However, according to these methods, necessary information may not sufficiently be provided in some situations. In those situations, it may take time to prepare for the imaging process or re-do the imaging process. There is a possibility that the patient and/or the tools may be positioned inappropriately in terms of safety, by mistake. Further, there is a possibility that it may take time to check certain information or that the operator may inadvertently forget certain information. Also, because the operator takes his/her eyes away from the patient when looking at a display device, there is a possibility that an unexpected accident may occur, when an imaging process is performed on a patient in an acute phase, or the like.

For these reasons, the MRI apparatus 100 according to the present embodiment is configured to be able to present procedures related to imaging processes more appropriately.

More specifically, in the present embodiment, the storage circuitry 12 stores therein workflow information indicating a series of procedures related to the imaging process. In this situation, the storage circuitry 12 is an example of the storage unit.

In this situation, the workflow information is information defining the series of procedures related to the imaging process. More specifically, with respect to the series of procedures related to the imaging process, the workflow information is information defining the contents of the work performed in each of the procedures and the order in which the work is performed. Further, the workflow information is stored in the storage circuitry 12 for each of various sites serving as imaging targets and for each of various imaging conditions such as imaging protocols, so that a corresponding piece of workflow information is read and used when an individual imaging process is performed.

For example, when the MRI apparatus 100 is shipped from a factory, the workflow information is created and stored into the storage circuitry 12. Alternatively, when the MRI apparatus 100 is installed in a hospital or the like, the workflow information may be created and stored into the storage circuitry 12. Further, when the MRI apparatus 100 starts being used, the workflow information may have additional information or may be corrected by an operator who is a radiologic technologist or the like.

Further, in the present embodiment, the processing circuitry 16 includes an analyzing function 16a and an informing function 16b. The analyzing function 16a is an example of the analyzing unit. The informing function 16b is an example of the informing controlling unit.

The analyzing function 16a is configured to analyze the image obtained by the camera 19.

More specifically, by analyzing the image obtained by the camera 19, the analyzing function 16a detects a positional arrangement and/or the state of at least one selected from among the MRI apparatus 100, the tools used for the imaging process, the patient S, and the operator. In this situation, examples of the tools used for the imaging process include an RF coil attached to the patient S (an RF coil dedicated for receiving, dedicated for transmitting, or used for both transmitting and receiving), a pad disposed between the patient S and the RF coil, a fixation tool used for setting the patient S onto the couch 9 (a belt, or the like), and a synchronization unit used for performing an imaging process in synchronization with a biological signal of the patient S. For example, the synchronization unit is realized with the ECG sensor 17 and the ECG circuitry 18.

In this situation, the state of the MRI apparatus 100, the tools used for the imaging process, the patient S, and the operator may be, for example, the position and movements of each of the imaged elements. For example, the analyzing function 16a detects the positions and movement of the operator, the patient S, and the tools used for the imaging process, each by analyzing the image obtained by the camera 19. For example, by using the moving image obtained by the camera 19, the analyzing function 16a detects the position and movements of the operator, the patient S, and the tools, each by calculating differences by comparing successive frames with one another. In another example, on the basis of shape data of the operator, the patient S, and the tool prepared in advance, the analyzing function 16a detects the position and movements of each of the imaged elements by recognizing characteristics of shapes and the like of the operator, the patient S, and the tools in each of the frames of the moving image obtained by the camera 19. In this situation, for example, the analyzing function 16a may detect the operator and the patient S while distinguishing one from the other, on the basis of colors of the clothes or the like.

On the basis of the workflow information stored in the storage circuitry 12 and a result of the analysis performed on the image by the analyzing function 16a, the informing function 16b is configured to identify a status of progress in the series of procedures defined by the workflow information and to provide information about an upcoming procedure through an informing device.

In the present embodiment, by using the projectors 20 as the informing device, the informing function 16b provides the information about the upcoming procedure by projecting a picture onto at least one selected from among the MRI apparatus 100, the tools used for the imaging process, the patient S, and the operator. Pith the present configuration in which the picture is projected by the projectors 20 in this manner, when two or more people work together, for example, the people are able to reference the projected information at the same time and to share the information with one another.

More specifically, the informing function 16b identifies the status of progress in the series of procedures, on the basis of the state of at least one selected from among the MRI apparatus 100, the tools used for the imaging process, the patient 2, and the operator detected by the analyzing function 16a. In another example, the informing function 16b identifies the status of progress in the series of procedures, by using at least one selected from among information about the MRI apparatus 100, information about the tools used for the imaging process, the imaging condition used for the imaging process, and information about the patient S.

Further, for each of the procedures included in the series of procedures, the informing function 16b judges whether or not the procedure is completed, and at the point in time when the procedure is completed, the informing function 16b provides information about the upcoming procedure. For example, as the information about the upcoming procedure, the informing function 16b provides information indicating a method recommended for the upcoming procedure. In this situation, examples of the recommended method include a method for improving the quality of the image to be taken and a method for better positioning the patient S that is required to safely carry out the imaging process, in accordance with positional arrangement information of the patient and the tools as well as the age, physique (height, weight, etc.), gender, and the like of the patient S.

Figure 2:
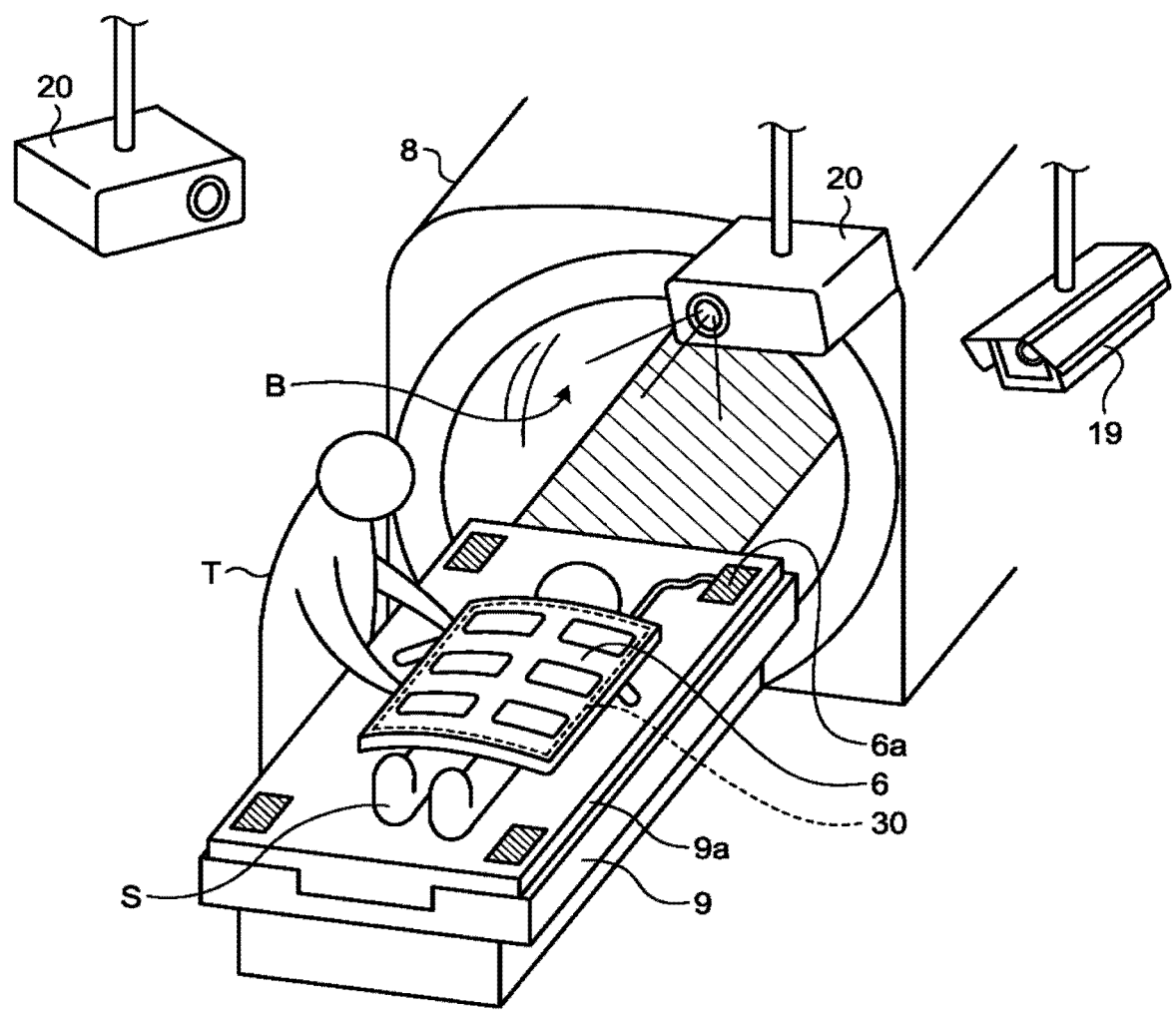
FIG. 2 is a drawing illustrating an example of a projecting process performed by an informing function according to the embodiment.

FIG. 2 is a drawing illustrating an example of the projecting process performed by the informing function 16b according to the present embodiment. For example, as illustrated in FIG. 2, when a procedure of arranging the receiver coil 6 to be used for the imaging process is performed on the patient S placed on the couchtop 9a of the couch 9, the informing function 16b projects, by using one or more of the projectors 20, an image 30 indicating the shape of the receiver coil 6 over the patient S, in an appropriate position where the receiver coil 6 should be arranged.

In this situation, for example, the informing function 16b identifies the site serving as an imaging target, on the basis of either order information transmitted thereto from a medical information system connected to the MRI apparatus 100 via a network or the imaging condition that was set. In this situation, the medical information system may be, for example, a Hospital Information System (HIS), a Radiology Information System (RIS), or the like. Further, the informing function 16b obtains an image of the receiver coil 6 corresponding to the identified imaging site, from among images of various types of receiver coils 6 stored in the storage circuitry 12. Alternatively, the informing function 16h may identify the position of the imaging site of the patient S, on the basis of the position of the patient S detected by the analyzing function 16a. After that, by using one or more of the projectors 20, the informing function 16b projects the obtained image of the receiver coil 6, by aligning the image into the identified position of the imaging site of the patient S.

After that, for example, while the operator T is actually performing the work of preparing and attaching the receiver coil 6 to the patient S, the informing function 16b identifies whether or not the receiver coil 6 is being arranged in the position onto which the image 30 was projected, on the basis of the position of the receiver coil 6 detected by the analyzing function 16a. After that, when having identified that the receiver coil 6 is arranged in the position onto which the image 30 was projected, the informing function 16b determines that the procedure of arranging the receiver coil 6 is completed.

In this situation, for example, the informing function 16b may identify that the receiver coil 6 has been arranged, by detecting coil connection information that is transmitted to the processing circuitry 16 when a connector 6a of the cable connected to the receiver coil 6 is connected to a connector of the couch 9. Alternatively, for example, the informing function 16b may identify that the receiver coil 6 has been arranged when the receiver coil 6 has been arranged in the position onto which the image 30 was projected, and also, the coil connection information of the receiver coil 6 is detected. In this manner, as a result of using both the position of the receiver coil 6 detected by the analyzing function 16a and the coil connection information in a combined manner, the informing function 16b is able to more accurately identify that the receiver coil 6 has been arranged.

Further, the informing function 16b judges safety appropriateness on the basis of the state of at least one selected from among the MRI apparatus 100, the tools used for the imaging process, the patient S, and the operator T and further issues a warning when having determined that the current situation is not appropriate. For example, the informing function 16b issues a warning when any of the tools used for the imaging process, the patient S, or the operator T is in a state described in an instruction manual of the MRI apparatus 100 or the tools as a matter that needs caution. For example, the informing function 16b issues a warning when the patient S is positioned in a prohibited state in which there is a possibility that he/she may get burned.

Further, in accordance with the position of the operator T detected by the analyzing function 16a, the informing function 16b switches the projector 20 used for providing the information to another projector 20 among the plurality of projectors 20. For example, in accordance with the position of the operator T, the informing function 16b selects such a projector 20 that is positioned so that the projection thereof is not to be blocked by the operator T, from among the plurality of projectors 20 and projects the picture by using the selected projector 20.

In this situation, the information provided by the informing function 16b is not limited to information acknowledged by the operator T, but may be information acknowledged by the patient S himself/herself. For example, as the information to be acknowledged by the patient S himself/herself, the informing function 16b may provide information about an appropriate position of the patient S so that the patient S is able to move at his/her own will.

The processing functions of the pieces of processing circuitry 13 to 16 have thus been explained. In the example illustrated in FIG. 1, the processing functions of the pieces of processing circuitry are each realized by a single piece of processing circuitry; however, possible embodiments are not limited to this example. Any of the processing functions of the pieces of processing circuitry may be realized as being distributed to a plurality of pieces of processing circuitry or being integrated into a single piece of processing circuitry.

Further, the processing functions of the pieces of processing circuitry 13 to 16 are stored in the storage circuitry 12 in the form of computer-executable programs, for example. By reading a corresponding one of the programs from the storage circuitry 12 and executing the read program, each of the pieces of processing circuitry realizes the processing function corresponding to the program. In other words, each of the pieces of processing circuitry 13 to 16 that has read the corresponding program has the corresponding one of the processing functions illustrated in FIG. 1.

Figure 3:
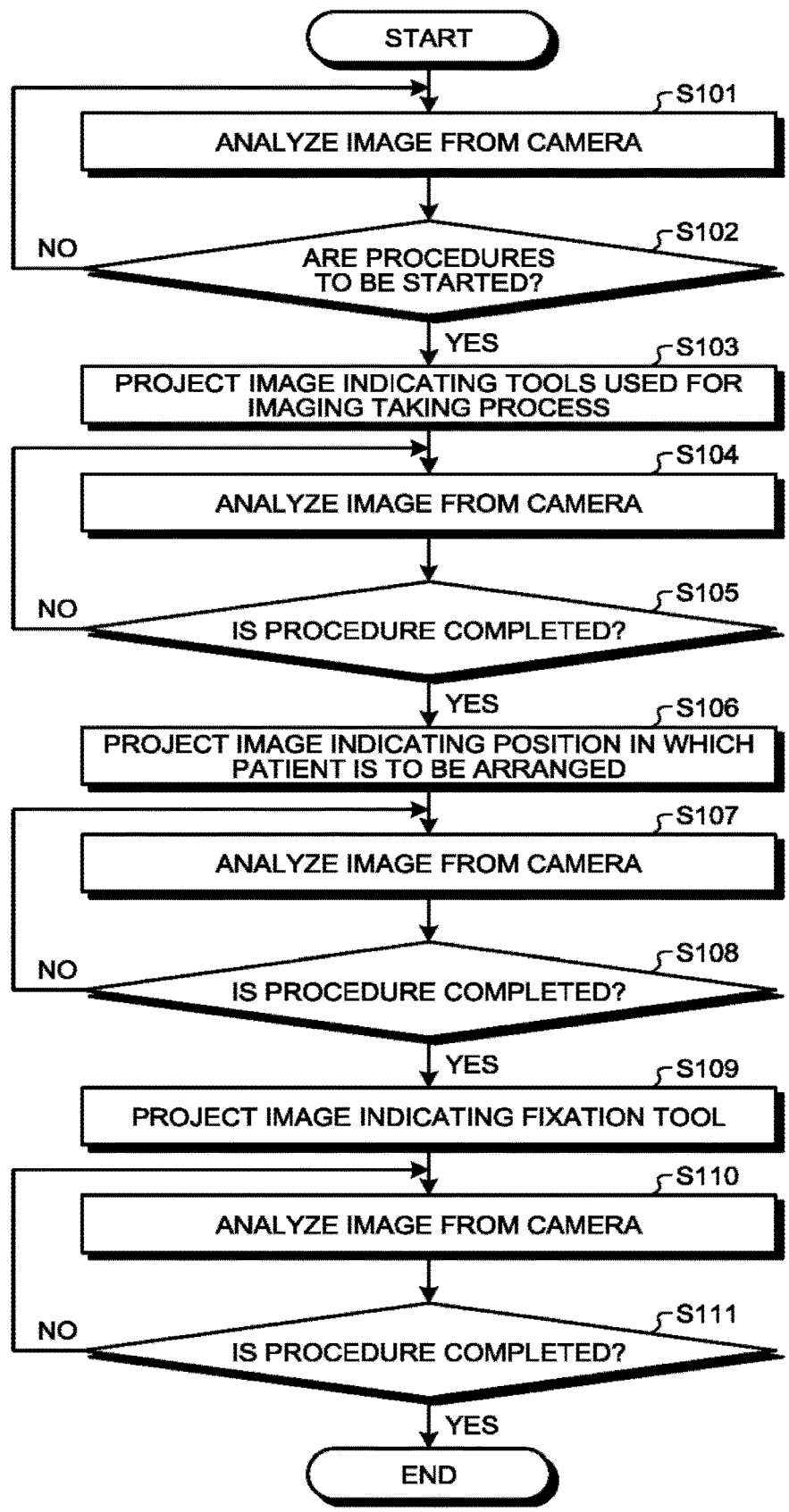
FIG. 3 is a flowchart illustrating an example of a process performed by the MRI apparatus according to the present embodiment.

FIG. 3 is a flowchart illustrating an example a process performed by the MRI apparatus 100 according to the present embodiment. An example will be explained in which the workflow information defines the order of the procedures as follows: a procedure of arranging the tools used for the imaging process such as the receiver coil 6 and a pad; a procedure of positioning the patient on the couch 9; and a procedure of setting the patient on the couch 9.

For example, as illustrated in FIG. 3, in the present embodiment, the analyzing function 16a at first analyzes an image obtained by the camera 19 (step S101). Further, the informing function 16b judges whether the procedures of the imaging process are to be started or not, on the basis of the workflow information and a result of the analysis performed on the image by the analyzing function 16a (S102).

In this situation, for example, when having identified that her the patient in the previous medical examination or the operator got away from the MRI apparatus 100, on the basis of the state of the patient and the operator detected by the analyzing function 16a, the informing function 16b determines that the procedures of the imaging process are to be started. Alternatively, when having identified that the tools used in the previous medical examination are removed from the MRI apparatus 100, on the basis of the state of the tools detected by the analyzing function 16a, the informing function 16b determines that the procedures of the imaging process are to be started. In another example, when detecting that an imaging condition for the next patient is set by the operator, the informing function 16b determines that the procedures of the imaging process are to be started.

Subsequently, when having determined that the procedures of the imaging process are to be started (step S102: Yes), the informing function 16b projects an image indicating the tools used for the imaging process onto the couchtop 9a of the couch 9 or the like (step S103).

After that, the analyzing function 16a continues to analyze the image obtained by the camera 19 (step S104). After that, on the basis of the workflow information and a result of the analysis performed on the image by the analyzing function 16a, the informing function 16b judges whether or not the procedure of arranging the tools to be used for the imaging process is completed (step S105).

In this situation, for example, on the basis of the state of the couchtop 9a and the tools detected by the analyzing function 16a, the informing function 16b identifies that the tools to be used for the imaging process are arranged on the couchtop 9a of the couch 9. After that, when having identified that the tools are arranged on the couchtop 9a of the couch 9, the informing function 16b determines that the procedure of arranging the tools to be used for the imaging process is completed.

After that, when having determined that the procedure of arranging the tools to be used for the imaging process is completed (step S105: Yes), the informing function 16b projects an image indicating the position in which the patient is to be arranged (i.e., positioned), onto the couchtop 9a of the couch 9 (step S106).

After that, the analyzing function 16a continues to analyze the image obtained by the camera 19 (step S107). Subsequently, on the basis of the workflow information and a result of the analysis performed on the image by the analyzing function 16a, the informing function 16b judges whether or not the procedure of positioning the patient on the couch 9 is completed (step S108).

In this situation, for example, on the basis of the state of the patient and the couchtop 9a detected by the analyzing function 16a, the informing function 16b identifies that the patient has been positioned on the couchtop 9a of the couch 9. After that, when having identified that the patient is positioned on the couchtop 9a, the informing function 16b determines that the procedure of positioning the patient on the couch 9 is completed. In this situation, for example, the informing function 16b may further judge safety appropriateness on the basis of the state of the MRI apparatus 100, the tools, the patient, and the operator detected by the analyzing function 16a. After that, when having determined that the current situation is appropriate in terms of safety, the informing function 16b may determine that the procedure of positioning the patient on the couch 9 is completed. On the contrary, when having determined that the current situation is not appropriate in terms of safety, the informing function 16b may issue a warning.

After that, when having determined that the procedure of positioning the patient on the couch 9 is completed (step S108: Yes), the informing function 16b projects an image indicating a fixation tool used for setting the patient on the couch 9, onto the couchtop 9a of the couch 9 or the like (step S109).

Subsequently, the analyzing function 16a continues to analyze the image obtained by the camera 19 (step S110). After that, on the basis of the workflow information and result of the analysis performed on the image by the analyzing function 16a, the informing function 16b judges whetper or not the procedure of setting the patient on the couch 9 is completed (step S111).

In this situation, for example, on the basis of the state of the patient, the couchtop 9a, and the fixation tool detected by the analyzing function 16a, the informing function 16b identifies that the patient set on the couch 9 by the fixation tool. After that, when having identified that the patient is mobilized on the couch 9 by the fixation tool, the informing function 16b determines that the procedure of setting the patient on the couch 9 is completed.

After that, when having determined that the procedure of setting the patient on the couch 9 is completed (step S111: Yes), the informing function 16b finishes the series of procedures defined by the workflow information. Subsequently, the patient is forwarded to the inside of the bore of the gantry 8 by the operator, and the imaging process is performed on the patient.

As explained above, in the present embodiment, the informing function 16b identifies the status of progress in the series of procedures, on the basis of the workflow information and the results of the analyses on the images performed by the analyzing function 16a and further predicts the information that is necessary in the upcoming procedure and provides the information thereof through the projectors 20.

Among the processing procedures described above, steps S101, S104, S107, and S110 are realized, for example, as a result of the processing circuitry 16 reading and executing a predetermined program corresponding to the analyzing function 16a from the storage circuitry 12. Further, steps S102, S103, S105, S106, S108, S109, and S111 are realized, for example, as a result of the processing circuitry 16 reading and executing a predetermined program corresponding to the informing function 16b from the storage circuitry 12.

As explained above, according to the present embodiment, the analyzing function 16a is configured to analyze the images obtained by the camera 19. Further, the informing function 16b is configured to identify the status of progress in the series of procedures on the basis of the workflow information indicating the series of procedures related to the imaging process and the results of the analyses performed on the images by the analyzing function 16a and is further configured to provide the information about the upcoming procedures by using the projectors 20.

More specifically, the storage circuitry 12 stores therein the workflow information indicating the plurality of procedures related to the preparation for the imaging process. For example, the storage circuitry 12 stores therein the workflow information indicating the plurality of procedures related to the preparation for the imaging process, including the procedure of arranging the RF coil and the fixation tools to be used for the imaging process. Further, the analyzing function 16a is configured to analyze the images obtained by the camera. Further, the informing function 16b is configured to identify which of the plurality of procedures has been performed on the basis of the workflow information and the results of the analyses performed on the images and to further cause the informing device to provide the information about the procedures corresponding to the identified results.

Further, for each of the plurality of procedures, the informing function 16b is configured to judge whether or not the procedure is completed and to cause the information to be provided at the point in time when each procedure is completed.

Further, the informing device is realized with the projectors. Further, the analyzing function 16a is configured to detect the position of the operator by analyzing the images. Further, the informing function 16b is configured to switch the projector used for projecting the information about the procedures, to another projector among the plurality of projectors, in accordance with the position of the operator.

Further, by analyzing the images, the analyzing function 16a is configured to detect the state of at least one selected from among the PRI apparatus 100, the tools used for the imaging process, the patient, and the operator. Further, on the basis of the state of at least one of these elements, the informing function 16b is configured to identify which one of the plurality of procedures has been performed.

Further, the informing function 16b is configured to identify which one of the plurality of procedures has been performed by using at least one selected from among the information about the MRI apparatus 100, the information about the tools used for the imaging process, the imaging condition used for the imaging process, and the information about the patient.

With these arrangements, it is possible to provide the operator and the patient with the information, in a manner that is visually easy to understand and in a timely fashion. The operator is thus able to perform the imaging process with more certainty and more easily. Further, the operator is able to acknowledge the information about the procedures of the manipulation without taking his/her eyes off the patient. Further, the information is appropriately presented, in accordance with the positional arrangements of the patient, the tools, and the like and the stages of the medical examination, without the operator being conscious of the situation. As a result, it is expected that the time period required by the entire imaging process can be shortened and that the occurrence of accidents can be prevented. Consequently, according to the present embodiment, it is possible to present the procedures related to the imaging process in a more appropriate manner.

MODIFICATION EXAMPLES

It is possible to carry out the embodiment described above by modifying a part of the functions of the MRI apparatus 100 as appropriate. Thus, modification examples of the embodiment above will be explained below.

For example, when the operator omits one or more of the procedures indeed in the series of procedures defined in the workflow information, the informing function 16b may provide information about the procedures, starting with the procedure following the one or more omitted procedures.

Figure 4:
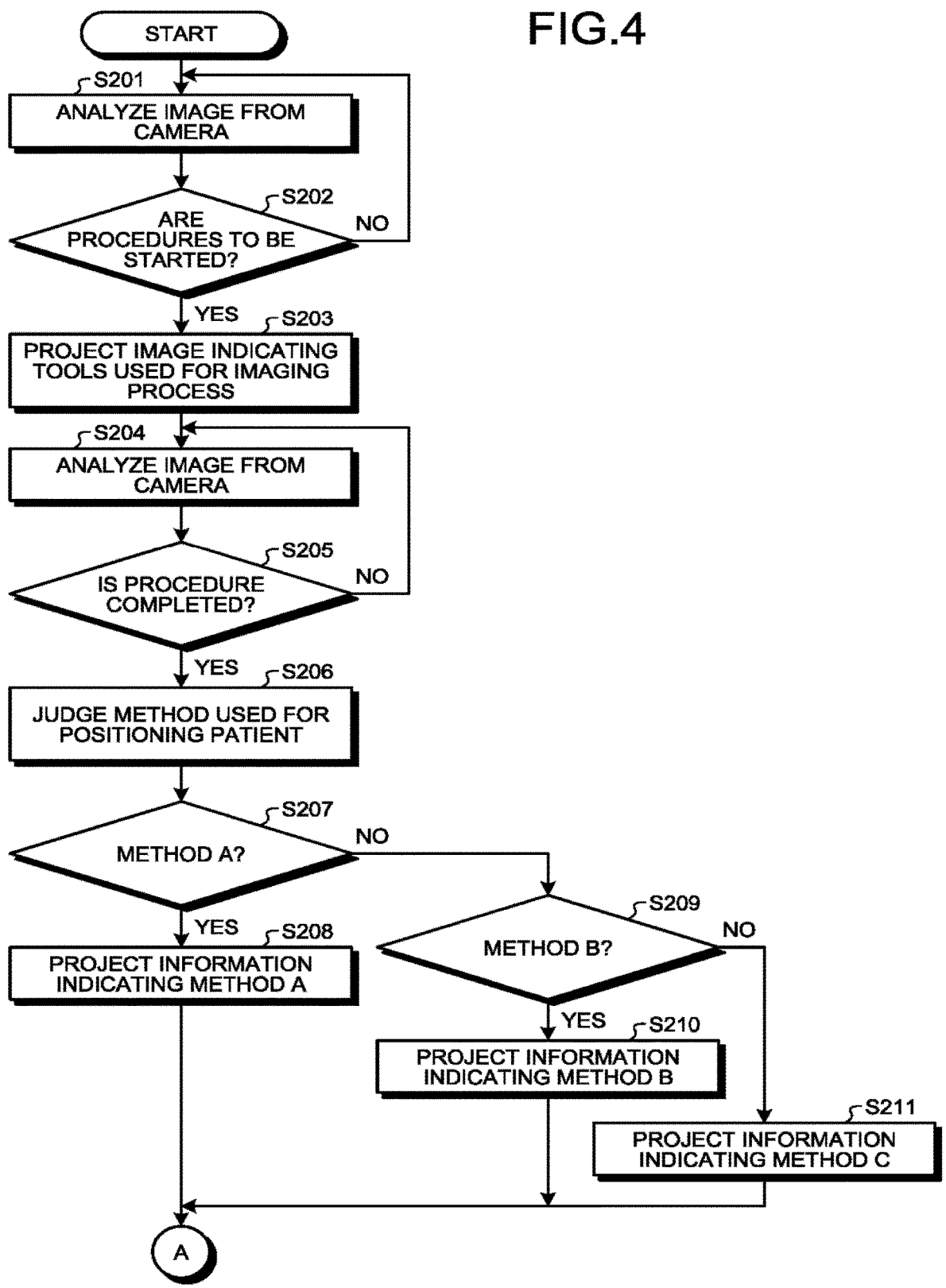
FIG. 4 is a flowchart illustrating an example of a process performed by an MRI apparatus according to a modification example of the present embodiment.

FIGS. 4 and 5 present a flowchart illustrating an example of the process performed by the MRI apparatus 100 according to a modification example of the present embodiment. Similarly to the example illustrated in FIG. 3, an example will be explained in which the workflow information defines the order of the procedures as follows: a procedure of arranging the tools (e.g., the receiver coil 6, a pad, etc.) used for the imaging process; a procedure of positioning the patient on the couch 9; and a procedure of setting the patient on the couch 9.

In this situation, the processes at steps S201 through S205 illustrated in FIG. 4 are the same as the processes at steps S101 through S105 illustrated in FIG. 3. Further, in the present modification example, when having determined that the procedure of arranging the tools used for the imaging process is completed (step S205: Yes), the informing function 16b judges a method for positioning the patient (step S206).

In this situation, for example, on the basis of either order information transmitted thereto from a medical information system or the imaging condition that was set, the informing function 16b identifies attributes of the patient such as his/her age, physique (height, weight, etc.), gender, and the like. After that, the informing function 16b determines a method for positioning the patient in accordance with the identified attributes of the patient. For example, in accordance with the physique of the patient, the informing function 16b determines the orientation and the position in which the patient is to be arranged, as well as the size, the type, and the like of the fixation tool to be used for setting the patient on the couch 9.

In this situation, for example, let us discuss an example in which methods A, B, and C are defined as methods for positioning the patient in correspondence with attributes of the patient. In that situation, when method A is specified as the method for positioning the patient (step S207: Yes), the informing function 16b projects information indicating method A onto one selected from among the MRI apparatus 100, the tools used for the imaging process, the patient, and the operator (step S208). For example, the informing function 16b projects an image indicating details of method A in a figure or text information describing details of method A by using text.

In contrast, when method B is specified as the method for positioning the patient (step S207: No and step S209: Yes), the informing function 16b projects information indicating method B (step S210). In another example, when method C is specified as the method for positioning the patient (step S209: No), the informing function 16b projects information indicating method C (step S211).

Subsequently, the analyzing function 16a continues to analyze the image obtained by the camera 19 (step S212). After that, on the basis of the workflow information and result of the analysis performed on the image by the analyzing function 16a, the informing function 16b judges whether the procedure of positioning the patient on the couch 9 is completed (step S213).

In this situation, in the present modification example, when having determined that the procedure of positioning the patient on the couch 9 is completed (step S213: Yes), the informing function 16b judges whether or not the operator has omitted one or more procedures.

More specifically, the analyzing function 16a continues to analyze the image obtained by the camera 19 (step S214). After that, on the basis of the workflow information and a result of the analysis performed on the image by the analyzing function 16a, the informing function 16b judges whether or not one or more procedures have been omitted by the operator (step S215).

In this situation, for example, when having determined that the procedure of positioning the patient on the couch 9 is completed and subsequently detecting that the patient is forwarded to the inside of the bore of the gantry 8, the informing function 16b determines that a procedure has been omitted by the operator.

Further, when having determined that one or more procedures have been omitted (step S215: Yes), the informing function 16b finishes the series of procedures defined by the workflow information. After that, the operator performs the imaging process on the patient.

On the contrary, when having determined that no procedure has been omitted (step S215: No), the informing function 16b projects an image indicating the fixation tool used for setting the patient on the couch 9, onto the couchtop 9a of the couch 9 or the like (step S216).

Subsequently, the analyzing function 16a continues to analyze the image obtained by the camera 19 (step S217). After that, on the basis of the workflow information and result of the analysis performed on the image by the analyzing function 16a, the informing function 16b judges whether or not the procedure of setting the patient on the couch 9 is completed (step S218).

After that, when having determined that the procedure of setting the patient on the couch 9 is completed (step 3218: Yes), the informing function 16b finishes the series of procedures defined by the workflow information. Subsequently, the operator forwards the patient to the inside of the bore of the gantry 8 and performs the imaging process on the patient.

As explained above, in the present modification example, when one or more of the procedures included in the series of procedures defined by the workflow information are omitted by the operator, the informing function 16b provides the information about the procedures, starting with the procedure following the one or more omitted procedures. Consequently, according to the present modification example, even when the operator has omitted one or more procedures, it is possible to present the information related to the imaging process more appropriately, in accordance with the actual contents of the work.

Further, for example, when the order of the series of procedures defined by the workflow information is changed by the operator, the informing function 16b may provide information about an upcoming procedure according to the order after the change.

For example, even when the same imaging process is performed on the head of the patient, there are a plurality of sets of procedures that are possible for the procedure of attaching the receiver coil 6 to the patient. For example, when an imaging process is performed on the head, generally speaking, in many situations, the head and the torso of the patient are each set on the couch 9. In those situations, there is one set of procedures in which the patient of the head is set and the torso is subsequently set. Another set of procedures is also acceptable in which the torso of the patient is set, and the head is subsequently set. Further, generally speaking, the receiver coil 6 used for imaging processes performed on the head is usually structured so as to be separated into a lower coil (a posterior coil) and an upper coil (an anterior coil). In that situation, there is one set of procedures in which the head of the patient is placed on the lower coil, before a pad is placed on the head, and subsequently, the upper coil is attached over the pad. Another set of procedures is also acceptable in which the head of the patient is placed on the lower coil, before the upper coil is attached over the head, and subsequently, the gap between the upper coil and the patient is filled with the pad.

Accordingly, for example, for each of the procedures included in the series of procedures defined by the workflow information, the informing function 16b judges whether or not the procedure scheduled to be an upcoming procedure is actually performed on the basis of the state of at least one selected from among the tools, the patient S, and the operator detected by the analyzing function 16a. Further, when having determined that a procedure different from the schedule is being performed, the informing function 16b accordingly changes the procedures thereafter and provides information according to the procedures after the change.

As explained above, according to the present modification example, when the order of the series of procedures defined by the workflow information is changed by the operator, the informing function 16b provides the information about the upcoming procedures according to the order after the change. Consequently, according to the present modification example, even when the operator changed the procedures, it is possible to more appropriately present the information related to the imaging process in accordance with the actual contents of the work.

Further, in the embodiments described above, the example is explained in which the informing device used for providing the information about the procedures is realized with the projectors 20; however, possible embodiments are not limited to this example.

For example, the informing device may be a head-mounted display attached to the head of the operator. In that situation, for example, the informing function 16b displays the image or the text information serving as the information indicating the procedures in a display region of the head-mounted display.

Alternatively, for example, the informing device may be a light emitting device having, on the couchtop 9a, a plurality of light emitting members arranged along the length direction or the width direction of the couchtop 9a. In that situation, for example, the informing function 16b provides the information about the position in which the patient or the receiver coil 6 is to be arranged, by causing one or more of the plurality of light emitting members to emit light.

In another example, the informing device may be a sounding device such as a speaker, a buzzer, a chime, or the like. In that situation, for example, when having identified that the patient or the receiver coil 6 has been arranged in an appropriate position, the informing function 16b provides a sound or voice indicating that the positional arrangement is completed, through the sounding device.

In yet another example, the informing device may be display such as a liquid crystal monitor, a Cathode Ray Tube (CRT) monitor, a touch panel, or the like provided for the gantry 8. In that situation, for example, the informing function 16b displays the image or the text information indicating the procedures on the display provided for the gantry 8.

Further, in the embodiments shove, the example is explained in which the informing function 16b identifies the status of progress in the series of work, on the basis of the results of the analyses performed on the images obtained by the camera 19; however, possible embodiments are not limited to this example. For instance, the informing function 16b may identify the status of progress by further using audio information obtained by a microphone.

More specifically, the informing function 16b identifies which of the plurality of procedures has been performed, by further using the audio information obtained by the microphone.

In that situation, for example, the informing function 16b detects voice of the operator and/or the patient via the microphone. After that, the informing function 16b identifies the status of progress in the series of work, by using, in a combined manner, the results of the analyses performed on the images obtained by the camera 19 and a result of the detection of the audio (voice) obtained by the microphone. For example, when having identified that one of the procedures is completed on the basis of a result of an analysis performed on an image obtained by the camera 19 and also having identified that mice indicating that the procedure is completed came from either the operator or the patient on the basis of a result of the detection of the audio (voice) obtained by the microphone, the informing function 16b determines that the procedure is completed.

Further, in the embodiments above, the example is explained in which the informing function 16b judges safety appropriateness on the basis of the state of at least one selected from among the tools used for the imaging process, the patient S, and the operator and further issues a warning when the informing function 16b determines that the current situation is not appropriate. However, possible embodiments are not limited to this example. For instance, when having determined that performing the imaging process is dangerous from a viewpoint of safety, the informing function 16b may prohibit performing the imaging process. For example, when a cable connected to the receiver coil 6 is arranged to form a loop, the informing function 16b prohibits the imaging process. In that situation, as a process to prohibit the imaging process, for example, the informing function 16b may provide, through an informing device, a message indicating that performing the imaging process is prohibited or may control any of the constituent elements included in the MRI apparatus 100 so as not to perform operations realizing the imaging process.

In the embodiments above, the examples with the MRI apparatus are explained; however, possible embodiments are not limited to those examples. For instance, it is possible to carry out the same embodiment with other types of medical image diagnosis apparatuses such as X-ray CT apparatuses, Positron Emission Tomography (PET) apparatuses, X-ray diagnosis apparatuses, ultrasound diagnosis apparatuses, and the like. In those situations, for example, a storage circuitry provided in a console or the like included in the medical image diagnosis apparatus is configured to store therein the workflow information described above, so that processing circuitry provided in the console or the like included in the medical image diagnosis apparatus is configured to have the analyzing function and the informing function described above.

The term "processor" used in the above embodiments denotes, for example, a Central Processing Unit (CPU), a Graphics Processing Unit (CPU), or a circuit such as an Application Specific integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the storage circuitry 12, it is also acceptable to directly incorporate the programs in the circuits of the processors. In that situation, the processors realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof.

In this situation, the programs executed by the processors are provided as being incorporated, in advance, in a Read-Only Memory (ROM), a storage circuitry, or the like. The programs may be provided as being recorded on a computer-readable storage medium such as a Compact Disk Read-Only memory (CD-ROM), a Flexible Disk (FD), a Compact Disk Recordable (CD-R), a Digital Versatile Disk (DVD), or the like, in a file using a format that is installable or executable in the device. Further, the programs may be provided or distributed as being stored in a computer connected to a network such as the Internet and being downloaded via the network. For example, the programs are each structured with a module including the functional units explained above. As for an actual hardware structure, as a result of a CPU reading and executing the programs from a storage medium such as a ROM, the modules are loaded into a main storage device and generated in the main storage device.

According to at least one aspect of the embodiments described above, it is possible to provide a medical image diagnosis apparatus and an MRI apparatus capable of more appropriately presenting tree procedures related to the imaging processes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
a gantry having a bore in which an imaged object is placed when an imaging process is performed on the imaged object;
storage circuitry configured to store therein workflow information defining contents and order of a plurality of works performed prior to the imaging process and performed manually to prepare the imaging process; and
processing circuitry configured to
analyze an image obtained by a camera before the imaged object is forwarded to inside of the bore of the gantry, the camera being different from an imaging device used for the imaging process, the image showing an outward appearance of the imaged object,
identify which of the plurality of works has been perfoliled on a basis of the workflow information and a result of the analysis performed on the image, and
cause an informing device to provide information about one or more of the works corresponding to a result of the identifying.

2. The medical image diagnosis apparatus according to claim 1, wherein, for each of the plurality of works, the processing circuitry judges whether or not the work is completed and causes the information to be provided at a point in time when each work is completed.

3. The medical image diagnosis apparatus according to claim 1, wherein
the informing device is realized with projectors,
the processing circuitry detects a position of an operator by analyzing the image, and
the processing circuitry switches a projector used for projecting the information about the works to another projector among the plurality of projectors, in accordance with the position of the operator.

4. The medical image diagnosis apparatus according to claim 1, wherein the camera is installed in at least one selected from among: an imaging room in which the medical image diagnosis apparatus is provided; a passage to the imaging room; and a room in which the preparation prior to the imaging process is performed.

5. The medical image diagnosis apparatus according to claim 1, wherein the processing circuitry causes the information to be projected a picture onto at least one of the medical image diagnosis apparatus, a tool used for the imaging process, a patient, and an operator.

6. The medical image diagnosis apparatus according to claim 1, wherein
by analyzing the image, the processing circuitry detects a state of at least one selected from among the medical image diagnosis apparatus, a tool used for the imaging process, a patient, and an operator, and the processing circuitry identifies which of the plurality of works has been performed, on a basis of the detected state of the selected.

7. The medical image diagnosis apparatus according to claim 6, wherein the processing circuitry judges safety appropriateness on the basis of the detected state of the selected and further issues a warning when having determined that a current situation is not appropriate.

8. The medical image diagnosis apparatus according to claim 1, wherein the processing circuitry identifies which of the plurality of works s has been performed by using at least one selected from among: information about the medical image diagnosis apparatus; information about a tool used for the imaging process; an imaging condition used for the imaging process; and information about a patient.

9. The medical image diagnosis apparatus according to claim 5, wherein the tool is a synchronization unit used for performing the imaging process in synchronization with a biological signal of the patient.

10. The medical image diagnosis apparatus according to claim 1, wherein
the processing circuitry detects a position of an operator by analyzing the image, and
the processing circuitry switches an informing device used for providing the information to another informing device among a plurality of informing devices, in accordance with the position of the operator.

11. The medical image diagnosis apparatus according to claim 1, wherein, when an operator omits one or more of the plurality of works, the processing circuitry causes the information to be provided, starting with a work following the one or more omitted works.

12. The medical image diagnosis apparatus according to claim 1, wherein, when the operator has changed order in which the plurality of works s are performed, the processing circuitry causes the information to be provided according to the order after the change.

13. The medical image diagnosis apparatus according to claim 1, wherein, as the information, the processing circuitry causes information indicating a method recommended for an upcoming work to be provided.

14. The medical image diagnosis apparatus according to claim 1, wherein the informing device is a head-mounted display attached to a head of an operator.

15. The medical image diagnosis apparatus according to claim 1, wherein the processing circuitry identifies which of the plurality of works has been performed by further using audio information obtained by a microphone.

16. A magnetic resonance imaging apparatus comprising:
a gantry having a bore in which an imaged object is placed when an imaging process is performed on the imaged object;
storage circuitry configured to store therein workflow information defining contents and order of a plurality of works performed prior to the imaging process and performed manually to prepare the imaging process, the plurality of works including a work of arranging an RF coil to be used for the imaging process; and
processing circuitry configured to
analyze an image obtained by a camera before the imaged object is forwarded to inside of the bore of the gantry, the camera being different from an imaging device used for the imaging process, the image showing an outward appearance of the imaged object,
identify which of the plurality of works has been performed on a basis of the workflow information and a result of the analysis performed on the image, and
cause an informing device to provide information about one or more of the works corresponding to a result of the identifying.

17. A magnetic resonance imaging apparatus comprising:
a gantry having a bore in which an imaged object is placed when an imaging process is performed on the imaged object;
storage circuitry configured to store therein workflow information defining contents and order of a plurality of works performed prior to the imaging process and performed manually to prepare the imaging process, the plurality of works including a work of arranging a pad to be used for the imaging process, the pad being used to fix a subject to be imaged; and
processing circuitry configured to
analyze an image obtained by a camera before the imaged object is forwarded to inside of the bore of the gantry, the camera being different from an imaging device used for the imaging process, the image showing an outward appearance of the imaged object,
identify which of the plurality of works has been performed on a basis of the workflow information and a result of the analysis performed on the image, and
cause an informing device to provide information about one or more of the works corresponding to a result of the identifying.

18. The medical image diagnosis apparatus according to claim 1, wherein the plurality of works include at least one of a work to arrange a tool to be used for the imaging process and a work to position a subject to be imaged on a couch.

19. The magnetic resonance imaging apparatus according to claim 16, wherein the object has been placed outside a bore when imaged such that the image obtained by the camera is the image showing the outward appearance of the object having been placed outside the bore.

20. The magnetic resonance imaging apparatus according to claim 17, wherein the object has been placed outside a bore when imaged such that the image obtained by the camera is the image showing the outward appearance of the object having been placed outside the bore.

* * * * *